Figure 4:
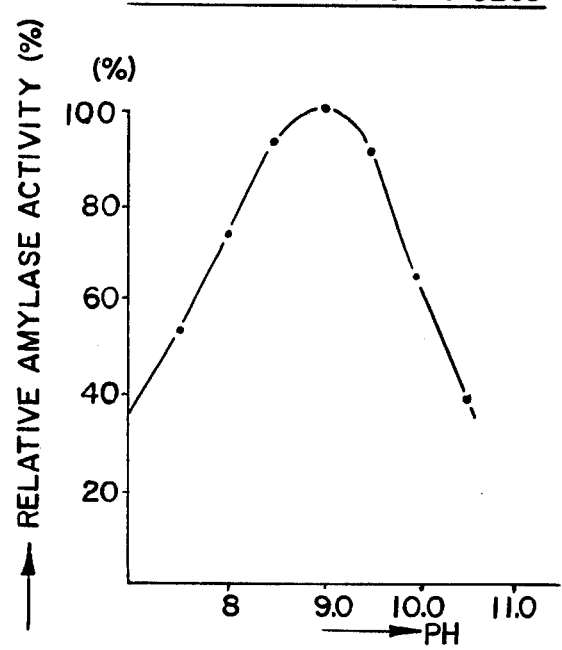

United States Patent [19]

Mitsugi et al.

[11] 4,022,666

[45] May 10, 1977

[54] ALPHA-AMYLASES FROM *BACILLUS SUBTILIS*

[75] Inventors: Koji Mitsugi, Kanagawa; Nobuo Kobayashi, Kawasaki; Toshiro Shida, Kawasaki; Yasunori Yokokawa, Kawasaki, all of Japan

[73] Assignee: Ajinomoto Co., Inc., Tokyo, Japan

[22] Filed: Sept. 9, 1970

[21] Appl. No.: 70,656

[30] Foreign Application Priority Data

Sept. 12, 1969 Japan .............................. 44-72386

[52] U.S. Cl. .............................. 195/62; 195/31 R; 195/63; 195/66 R; 195/68; 252/DIG. 12
[51] Int. Cl.² ......................................... C07G 7/02
[58] Field of Search ............ 195/62 R, 63 R, 66 R, 195/68, 31 R; 252/DIG. 12

[56] References Cited

OTHER PUBLICATIONS

Campbell; L. L., Arch of Biochem and Biophys, vol. 54, pp. 154–161.
Nishida et al., Agr. Biol. Chem. vol. 31, pp. 682–693, 1967.
Radley; J. A., Starch and its Derivatives 4th Ed., p. 437, Published by Chapman and Hall, 1968.

*Primary Examiner*—David M. Naff
*Attorney, Agent, or Firm*—Hans Berman

[57] ABSTRACT

Alpha-amylases which have optimum activity between pH 6.5 to 8 and between pH 9.0 to 11.5 at 40° C are produced by culturing strains of *Bacillus subtilis* on a nutrient medium under aerobic conditions. Some of the alpha amylases are effective in hot and alkaline detergent solutions containing chelating agents.

6 Claims, 5 Drawing Figures

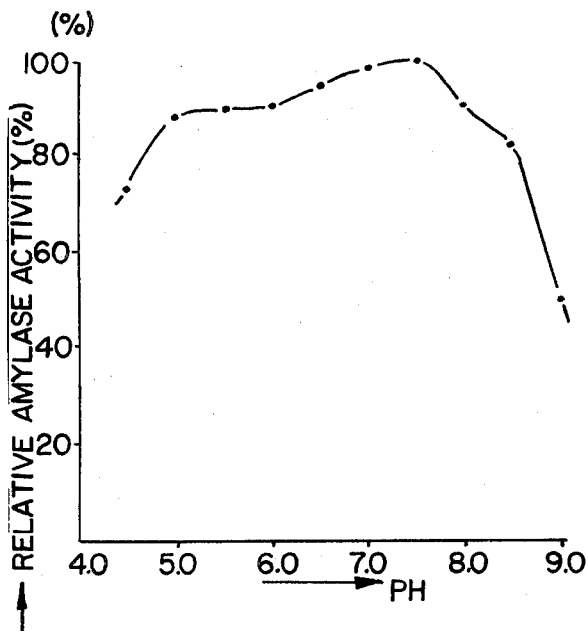
FIG.IA — OPT PH OF AMYLASE PRODUCED BY BACILLUS SUBTILIS AJ 3250
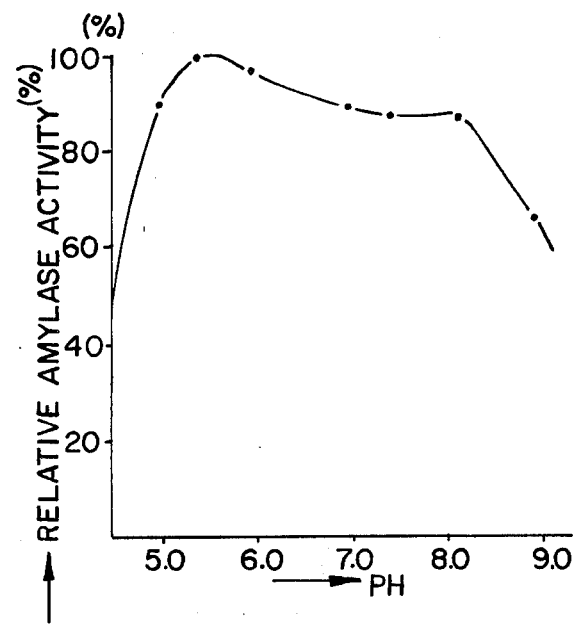
FIG.IB — OPT PH OF AMYLASE PRODUCED BY BACILLUS SUBTILIS AJ 3252
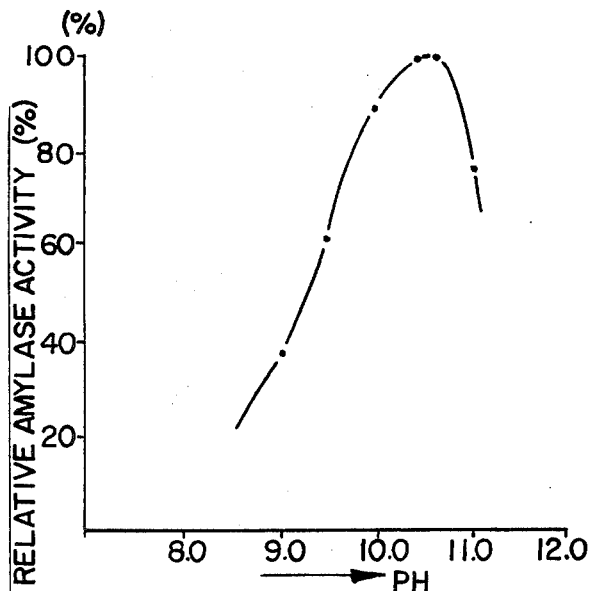
FIG.2 — OPT PH OF AMYLASE PRODUCED BY BACILLUS SUBTILIS AJ 3298
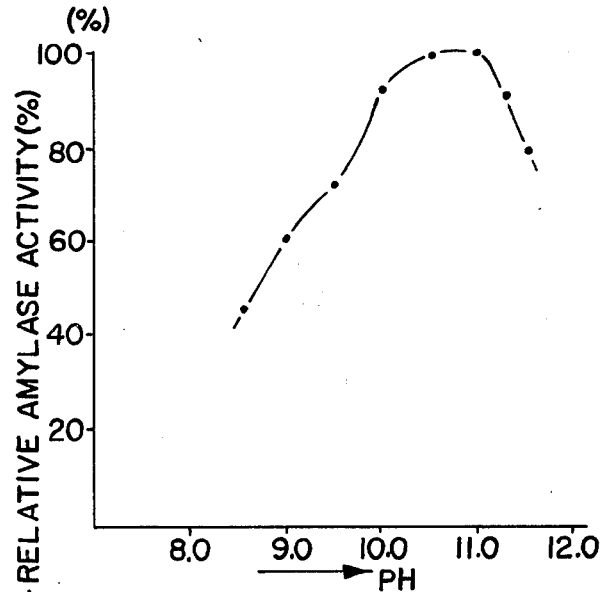
FIG.3 — OPT PH OF AMYLASE PRODUCED BY BACILLUS SUBTILIS AJ 3299

ALPHA-AMYLASES FROM *BACILLUS SUBTILIS*

This invention relates to novel amylases and to the preparation thereof by bacteria.

Various amylases have been isolated from animal and plant bodies since Kohn and Ohlsson's work of the nineteentwenties, and some of the amylases are used industrially. All known amylases are effective in acidic or neutral media, and an amylase effective in an alkaline medium has never been known.

It has now been found that α-amylases effective in neutral and alkaline media can be produced by culturing bacteria belonging to the genus Bacillus on a nutrient medium under aerobic conditions.

Amylases which can be obtained according to the present invention include neutral α-amylases of optimum amylolytic activity at 40° C at a pH between 6.5 and 8, and alkaline α-amylases whose optimum pH is between 9.0 and 11.5 at 40° C.

Bacteria which produce these new types of amylases include Bacillus subtilis AJ-3249, Bacillus subtilis AJ-3250 (FERM P-374), Bacillus subtilis AJ-3252 (FERM P-375), Bacillus subtilis AJ-3255 (FERM P-376), Bacillus subtilis AJ-3298 (FERM P-660) and Bacillus subtilis AJ-3299 (FERM P-661). Microorganisms identified by FERM-P numbers are available to the public from the Fermentation Research Institute, Agency of Industrial Science and Technology, of the Ministry for Industrial Trade and Industry, Japan.

The bacteria are cultured on a medium containing as assimilable carbon source, an assimilable nitrogen source, inorganic salts and organic nutrients. The assimilable carbon sources include carbohydrates such as glucose, starch, dextrin or maltose, and organic acids such as acetic acid. Assimilable nitrogen sources are inorganic ammonium salts such as ammonium chloride, ammonium sulfate or ammonium nitrate, and organic nitrogen compounds such as soybean cake, soybean powder, milk casein, peptone, milk whey, meat extracts and amino acids.

The cultivation is carried out at a temperature between 25° and 45° C, preferably between 30° and 40° C, under aerobic conditions by shaking, stirring and/or aerating. The best pH of the culture medium varies with the strain used. Bacillus subtilis AJ-3249, AJ-3250 (FERM P-374) and AJ-3252 (FERM P-375) are cultured at pH 6.5 to 8.0, *Bacillus subtilis AJ-3255* (FERM P-376) is cultured at pH of 8.0 to 10.0, and *Bacillus subtilis* AJ-3298 (FERM P-660) and AJ-3299 (FERM P-661) are cultured at a pH between 9.0 and 10.5.

In order to isolate the neutral and/or alkaline amylase produced in the culture medium, the bacterial cells are removed by centrifuging or filtration, the amylase is precipitated by adding inorganic salts, such as ammonium sulfate or sodium sulfate, and/or organic solvents such as ethanol or acetone. The precipitate can be recovered by centrifuging or filtration. Ion exchange resins may also be used for purification and isolation.

Amylases produced according to the present invention are useful for many purposes. The crude amylases are useful in protease containing laundry compositions. They are also useful for decomposing insoluble starch waste discharged from card-board factories and consisting of alkaline paste. In the appended drawing, FIGS. 1A, 1B, 2, 3, and 5 are diagrams of the relationship between pH and the enzyme activities of respective amylases of the invention in aqueous solutions.

α-amylase activity was determined by a variation of Wohlgemuth's method in which 9 ml of M/10 phosphate buffer (pH 7.0) or M/10 borate buffer (Atkins-Pantin buffer) (pH 9.5) containing 0.65 g/dl soluble starch was mixed with 1 ml of enzyme solution, and the mixture was statically incubated at 40° C. A one milliliter sample was taken at intervals and was added to a mixture consisting of 4 ml of 0.44M-trichloroacetic acid and 3 ml of N/1000 $I_2$-KI solution, and the time at which the optical density of the reaction mixture was 0.300 at 660 mμ was measured.

$$\text{Unit/ml} = \frac{10 \text{ minutes}}{\text{minutes for O.D. being 0.300 at 660 m}\mu} \times 10 \times \text{dilution of enzyme solution}$$

One unit was defined as the amylolytic activity which decomposes 6.0 mg soluble starch in 10 minutes.

PROPERTIES OF AMYLASES

Amylases produced by Bacillus subtilis AJ-3249, AJ-3250 (FERM P-374) and AJ-3252 (FERM P-375) have the following properties.

1. The optimum pH is to 6.5 to 8.0 at 40° C, as shown in FIGS. 1A and 1B.
2. The enzyme is still effective when heated at 50° C for 60 minutes.
3. The enzymes are stable at a pH 5.5 to 9.0.
4. Glucose, maltose and dextrin are produced by hydrolysis of starch by the amylase over a prolonged period, and 80% of the charged starch is decomposed.
5. The amylases are not inactivated by chelating agents such as sodium tripolyphosphate (TPP), EDTA and sodium nitrilotriacetate (NTA), as shown in Table 1. The Table lists residual amylase activity in percent of the initial activity. In each test, 100 units per milliliter of pure enzyme solution and 100 mg of TPP (50 mg EDTA or 50 mg NTA) were dissolved in 50 ml of 0.03M-barbitalacetate buffer solution (pH 7.0), and the reaction mixture was incubated at 50° C.

Table 1

| Enzyme | Chelating agent | Activity after minutes (%) | | | | |
|---|---|---|---|---|---|---|
| | | 0 | 10 | 20 | 30 | 60 |
| Spitase CP-3 | TPP | 100 | 34 | 0 | 0 | 0 |
| Kleistase M-20 | TPP | 100 | 35 | 0 | 0 | 0 |
| Amylase of AJ-3250 | TPP | 100 | 98 | 95 | 93 | 90 |
| Amylase of AJ-3250 | EDTA | 100 | 95 | 92 | 89 | 80 |
| Amylase of AJ-3250 | NTA | 100 | 97 | 95 | 91 | 85 |

Spitase of CP-3: Commercial amylase produced by Nagase & Co., Ltd., Osaka, Japan
Kleistase M-20: Commercial amylase produced by Daiwa Kasei Co., Ltd., Osaka, Japan Alkaline amylase of Bacillus subtilis AJ-3298 (FERM P-660) has the following properties.

1. The optimum pH is 10.0 to 10.7, as shown in FIG. 2. FIG. 2 shows relative amylase activity against maximum activity. In each test, 100 units per milliliter of pure enzyme was dissolved in 50 ml of 0.1M-borate buffer (pH 9.0 – 11.00 and the reaction mixture was incubated at 40° C for 10 minutes.
2. The enzyme is stable at pH between 7.0 and 10.0, as shown in Table 2. In each test, a mixture of 100 units per ml of enzyme solution and M/25 -Britton-Robinson buffer solution was incubated at 30° C for 24 hours at a pH as indicated in the Table, and residual enzyme activity was determined at pH 9.5 (0.1M-borate buffer).

Table 2

| Residual enzyme activity (%) at pH | | | | | | |
|---|---|---|---|---|---|---|
| 5.0 | 6.0 | 7.0 | 8.0 | 9.0 | 10.0 | 11.0 |
| 0 | 10 | 75 | 83 | 92 | 88 | 0 |

3. The enzyme is stable in the presence of chelating or commercial detergents, as shown in Table 3. 100 Units per milliliter of the enzyme solution was incubated at 50° C in the presence of 1/100 molar calcium ions, 2 g/dl TPP or 0.2 g/dl "Tide" (commercially available detergent of Procter and Gamble Co., U.S.A.).

Table 3

| In the presence of | Residual enzyme activity after minutes (%) | | | |
|---|---|---|---|---|
| | 0 | 10 | 20 | 30 |
| none | 100 | 83 | 80 | 70 |
| Ca$^{++}$ | 100 | 100 | 100 | 90 |
| TPP | 100 | 86 | 74 | 63 |
| Tide | 84 | 25 | 5 | 0 |

Alkaline amylase of Bacillus sp AJ-3299 (FERM P-661) has the following properties. Each test was preformed in the same procedure as of the amylase of Bacillus subtilis AJ-3298.

1. The optimum pH is 10.0 to 11.5, as shown in FIG. 3.
2. The stability of the enzyme is shown in Table 4.

Table 4

| Residual enzyme activity (%) at pH | | | | | | | |
|---|---|---|---|---|---|---|---|
| 6.0 | 7.0 | 8.0 | 8.5 | 9.0 | 10.0 | 10.5 | 11.0 |
| 0 | 21 | 80 | 95 | 90 | 70 | 5 | 0 |

3. Residual enzyme activity when incubated in the presence of various ions is listed in Table 5.

Table 5

| In the presence of | Residual enzyme activity (%) after minutes | | | |
|---|---|---|---|---|
| | 0 | 10 | 20 | 30 |
| none | 100 | 70 | 55 | 42 |
| Ca$^{++}$ | 100 | 75 | 60 | 55 |
| TPP | 100 | 10 | 0 | 0 |
| TPP and Ca$^{++}$ | 100 | 75 | 60 | 58 |
| Tide | 100 | 0 | 0 | 0 |
| Tide and Ca$^{++}$ | 100 | 40 | 32 | 20 |

Alkaline amylase of *Bacillus subtilis* AJ-3255 (FERM P-376) has the following properties.

1. The optimum pH is 9.0 at 40° C, as shown in FIG. 4.
2. The enzyme is effective between pH 6.0 and 11.0 at 40° C. The enzyme activity was determined in the same way as that of *Bacillus subtilis* AJ-3298.
3. Residual enzyme activity when incubated in the presence of calcium ions or TPP is listed in Table 6.

Table 6

| In the presence of | Residual enzyme activuty (%) after minutes | | | |
|---|---|---|---|---|
| | 0 | 10 | 20 | 30 |
| none | 100 | 90 | 80 | 60 |
| Ca$^{++}$ | 100 | 98 | 95 | 94 |
| TPP | 100 | 20 | 0 | 0 |

EXAMPLE 1

A culture medium consisting of 1 g/dl of soybean cake extracts (as dry matter), 1 g/dl polypeptone and 8 g/dl soluble starch, of pH 7.0 was prepared, each 50 ml batch of the medium was placed in a 500 ml shaking flask, and sterilized at 120° C for 20 minutes. The medium was inoculated with a of Bacillus subtilis AJ-3250 (FERM P-374) which had previously been cultured on an agar slant consisting of 2 g/dl soluble starch, 1 g/dl yeast extracts, 1 g/dl polypeptone and 0.5 g/dl NaCl at 34° C for 24 hours, and cultured at 34° C for 96 hours with shaking. The culture broth was found to contain 2500 units/ml amylase at pH 7.0. 930 Ml of the culture broth collected from 20 flasks was centrifuged to remove bacterial cells, 365 g solid ammonium sulfate was added to the 850 ml of supernatant liquid, and the solution was left to stand overnight with cooling. Amylase precipitated and was collected by centrifuging at 10,000 r.p.m. for 20 minutes, and dried in vacuo overnight with cooling, a crude enzyme powder containing 360,000 units/g of amylase was obtained in an amount of 51.0 g (isolation yield: 87%).

EXAMPLE 2

A culture medium containing 4 g/dl defatted soybean powder and 5 g/dl starch, was prepared (pH 7.0), 50 ml of the medium was inoculated with *Bacillus subtilis* AJ-3249, and cultured at 34° C for 96 hours with shaking. The culture broth contained 1950 units/ml of amylase at pH 7.0.

900 Ml of the broth was treated in the same way as in Example 1, and yielded a crude enzyme powder containing 52,000 units/g of amylase and weighing 28 g (isolation yield: 80%).

EXAMPLE 3

*Bacillus subtilis* AJ-3252 (FERM P-375) was cultured on a medium containing 1 g/dl polypeptone, 1 g/dl meat extracts and 5 g/dl soluble starch (pH 8.0) at 37° C for 120 hours, and the culture broth was found to contain 2,100 units/ml of amylase at pH 7.0.

EXAMPLE 4

A culture medium containing 5 g/dl potato starch, 0.3 g/dl polypeptone and 1 g/dl sodium carbonate was prepared (pH 10.5), and 20 ml of the medium was placed in a test tube. The medium was inoculated with a of Bacillus subtilis AJ-3255 (FERM P-376) which had previously been cultured on an agar slant containing 2 g/dl soluble starch, 0.5 g/dl sodium nitrilotriacetate, 1 g/dl polypeptone, 1 g/dl yeast extracts, 0.5 g/dl NaCl and 2 g/dl agar (pH 8.0) at 30° C for 27 to 48 hours, and cultured at 30° C for 76 hours with shaking. The culture broth was found to contain 110 units/ml of amylase at pH 10.0.

Culture broths were collected from 50 test tubes, 870 ml of the broth was centrifuged to remove bacterial cells at 10,000 r.p.m. for 10 minutes, and to the supernatant (720 ml), 337 g of solid ammonium sulfate was added. The resulting solution was cooled in an ice box overnight, the precipitate formed was isolated by centrifuging at 10,000 r.p.m. for 20 minutes, and dried in vacuo to yield 3.79 g of crude amylase powder containing 16,700 units/g of amylase (isolation yield: 80%).

EXAMPLE 5

*Bacillus substilis* AJ-3255 (FERM P-376) was cultured on a medium containing 8 g/dl soluble starch, 1 g/dl polypeptone and 1 g/dl soybean cake extracts at pH 10.0, at 30° C for 96 hours with shaking. The culture broth was found to contain 350 units/ml of amylase at pH 9.5. 1150 ML of the culture broth was treated in the same way as in Example 4, and 7.56 g (isolation yield: 89%) of crude enzyme powder which contained 40,100 units/g of amylase was obtained.

EXAMPLE 6

A culture medium containing 5 g/dl corn starch, 1 g/dl polypeptone, 1 ml/dl "Aji-Eki" (Brand Name of soybean protein hydrolyzate), 0.05 g/dl $KH_2PO_4$ and 0.02 g/dl $MgSO_4·7H_2O$ was cultured with Bacillus subtilis AJ-3298 (FERM P-660) which had previously been cultured on an agar slant containing 2 g/dl soluble starch, 1 g/dl polypeptone, 1 g/dl yeast extracts, 0.5 g/dl NaCl and 2 g/dl agar (pH 9.5), at pH 9.5, at 34° C for 60 hours with shaking. The pH of the medium was maintained at 9.5 by adding ammonia water. The culture broth was found to contain 120 units/ml of amylase at pH 10.5.

800 ML of the culture broth was treated in the same way as in Example 4, and 3.5 g of crude enzyme powder which contained 19,000 units/g of amylase was obtained (isolation yield: 79.3%).

EXAMPLE 7

*Bacillus subtilis* AJ-3299 (FERM P-661) was cultured on a medium containing 8 g/dl soluble starch, 2 g/dl meat extracts, 2 g/dl polypeptone, 0.25 g/dl NaCl, 0.5 g/dl soybean cake extracts and 1 g/dl sodium carbonate (pH 9.5) at 34° C for 96 hours with shaking. The culture broth was found to contain 250 units/ml of amylase at pH 10.5.

From 2100 ml of culture broth, 13.4 g of crude enzyme powder which contains 25,000 units/g of amylase was obtained (isolation yield: 74.7%).

What we claim is:

1. Microbial α-amylase having optimum amyloltyic acitivity at 40° C and at a pH value between 9.0 and 11.5.

2. α-Amylase as set forth in claim 1, having said optimum activity at a pH value of at least 10.0.

3. α-Amylase as set forth in claim 1, having said optimum activity at a pH value between 10.0 and 10.7.

4. α-Amylase as set forth in claim 1, having said optimum activity at a pH value of approximately 9.0.

5. A method of producing an α-amylase as defined in claim 1, which comprises culturing a bacterium of the species *Bacillus subtilis* capable of producing alkaline amylase on an aqueous nutrient medium containing assimilable sources of carbon and nitrogen, inorganic salts, and minor organic nutrients at a pH between 8.0 and 10.5, until said α-amylase accumulates in said medium, and recovering the accumulated α-amylase.

6. A method as set forth in claim 5, wherein said bacterium is *Bacillus substilis* FERM P-660, FERM P-661 or FERM P-376.

* * * * *

UNITED STATES PATENT AND TRADEMARK OFFICE
CERTIFICATE OF CORRECTION

PATENT NO. : 4,022,666

DATED : May 10, 1977

INVENTOR(S) : Koji Mitsugi et al.

It is certified that error appears in the above—identified patent and that said Letters Patent are hereby corrected as shown below:

Claim 1, line 1, change "amyloltyic" to -- amylolytic --.

Signed and Sealed this second Day of August 1977

[SEAL]

Attest:

RUTH C. MASON
Attesting Officer

C. MARSHALL DANN
Commissioner of Patents and Trademarks